(12) United States Patent
Walker et al.

(10) Patent No.: US 6,194,216 B1
(45) Date of Patent: Feb. 27, 2001

(54) METHOD FOR DETERMINATION OF AMINE-BASED ADDITIVES IN DRILLING FLUID FILTRATES

(75) Inventors: Nyal S. Walker; Michael A. Jarrett; Dennis K. Clapper, all of Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/506,074

(22) Filed: Feb. 16, 2000

(51) Int. Cl.[7] .................................................. G01N 31/00
(52) U.S. Cl. .............................. 436/60; 436/111; 436/27; 436/172; 250/255; 73/152.23
(58) Field of Search .............................. 436/60, 113, 111, 436/27, 172; 250/255; 73/152.23

(56) References Cited

U.S. PATENT DOCUMENTS

| | | | |
|---|---|---|---|
| 2,606,818 | * | 8/1952 | Spring et al. . |
| 3,044,860 | * | 7/1962 | Verley .................................. 436/60 |
| 3,635,677 | * | 1/1972 | Drake, Jr. et al. ..................... 436/60 |
| 4,659,676 | * | 4/1987 | Rhyne, Jr. ............................. 436/56 |
| 4,699,002 | | 10/1987 | Rockley . |
| 4,805,708 | | 2/1989 | Matza et al. . |
| 4,840,910 | | 6/1989 | Matza et al. . |
| 5,161,409 | | 11/1992 | Hughes et al. . |
| 5,254,531 | | 10/1993 | Mueller et al. . |
| 5,360,738 | * | 11/1994 | Jones et al. ............................ 436/30 |
| 5,729,342 | | 3/1998 | Yokoyama et al. . |
| 5,858,798 | | 1/1999 | Godfrey et al. . |

OTHER PUBLICATIONS

ESP@CENET Database Abstract of DE 3881695 Jul. 15, 1993, Abstract date Apr. 12, 2000.

\* cited by examiner

Primary Examiner—Jacqueline V. Howard
(74) Attorney, Agent, or Firm—Madan, Mossman & Sriram, P.C.

(57) ABSTRACT

The invention concerns a method for determining the presence and quantity of an amine-based additive in fluids, particularly aqueous fluids used in hydrocarbon recovery such as drilling fluids, drill-in fluids, completion fluids, and the like. It was discovered that, after isolating the amine-based additive, the amount of clay stabilizer is linearly dependent upon the spectrometric count of its peak fluorescent spectrum. The method is reproducible and is not bothered by the presence of lignosulfonate and/or lignite which interferes with conventional methods.

18 Claims, 4 Drawing Sheets

METHOD FOR DETERMINATION OF AMINE-BASED ADDITIVES IN DRILLING FLUID FILTRATES

FIELD OF THE INVENTION

The present invention relates to methods for determining the presence and proportion of certain additives in drilling fluids, and more particularly relates, in one embodiment, to methods for determining the presence and proportion of amine-based additives in drilling fluid filtrates.

BACKGROUND OF THE INVENTION

Drilling fluids used in the drilling of subterranean oil and gas wells as well as other drilling fluid applications and drilling procedures are known. In rotary drilling there are a variety of functions and characteristics that are expected of drilling fluids, also known as drilling muds, or simply "muds". The drilling fluid is expected to carry cuttings up from beneath the bit, transport them up the annulus, and allow their separation at the surface while at the same time the rotary bit is cooled and cleaned. A drilling mud is also intended to reduce friction between the drill string and the sides of the hole while maintaining the stability of uncased sections of the borehole. The drilling fluid is formulated to prevent unwanted influxes of formation fluids from permeable rocks penetrated and also often to form a thin, low permeability filter cake which temporarily seals pores, other openings and formations penetrated by the bit. The drilling fluid may also be used to collect and interpret information available from drill cuttings, cores and electrical logs. It will be appreciated that within the scope of the claimed invention herein, the term "drilling fluid" also encompasses "drill-in fluids" and "completion fluids".

Drilling fluids are typically classified according to their base material. In water-based muds, solid particles are suspended in water or brine. Oil can be emulsified in the water. Nonetheless, the water is the continuous phase. Oil-based muds are the opposite. Solid particles are suspended in oil, and water or brine is emulsified in the oil and therefore the oil is the continuous phase. Oil-based muds which are water-in-oil emulsions are also called invert emulsions. Brine-based drilling fluids, of course are a water-based mud in which the aqueous component is brine.

Special problems occur when drilling into certain formation types, such as shale which contain clays. Clay particles will hydrate (absorb water) and interfere with drilling operations by causing bit balling and other problems. It is thus customary when using aqueous-based drilling fluids in dispersive shale formations to include a clay stabilizer additive (or shale stabilizer) to control clay hydration and disintegration during drilling. The clay stabilizer additive is to inhibit the dispersion and wetting, and thus swelling tendencies, of drilled clay particles. Ideally the clay stabilizer additive coats the drilled particles immediately after they are drilled to inhibit water from penetrating and swelling the clays within the shale. Clay stabilizer additives also aid in friction reduction and improving lubricity.

However, clay stabilizers are like many drilling fluid additives in that they are relatively expensive. It would be desirable to be able to determine how much clay stabilizer is present within a drilling mud so that there is enough present to be effective, but not so much that excessive amounts are being wasted. The same considerations would be true for other additives to drilling, drill-in, and completion fluids which would include corrosion inhibitors, surfactants, and the like.

In general, it is apparent to those selecting or using a drilling fluid for oil and/or gas exploration that an essential component of a selected fluid is that it be properly balanced to achieve all of the necessary characteristics for the specific end application. Because the drilling fluids are called upon to do a number of tasks simultaneously, this desirable balance is not always easy to accomplish, nor is it easy to achieve in the most economical fashion possible.

It would be desirable if compositions and methods could be devised to aid and improve the ability of drilling fluids to simultaneously accomplish these tasks.

SUMMARY OF THE INVENTION

Accordingly, it is an object of the present invention to provide a method to determine the presence of an amine-based additive in a fluid used for hydrocarbon recovery, such as a drilling fluid, drill-in fluid, and/or completion fluid, and the like.

It is another object of the present invention to provide a method to determine the quantity of an amine-based additive in a fluid used in hydrocarbon recovery.

Still another object of the invention is to provide a method for determining the presence and quantity of an amine-based additive in a drilling fluid used for hydrocarbon recovery, even in the presence of lignite and/or lignosulfonate.

In carrying out these and other objects of the invention, there is provided, in one form, a method for determining the quantity of amine-based additive in an aqueous fluid involving first isolating the amine-based additive from a drilling fluid filtrate sample and then placing the amine-based additive in a cuvette. Next, the amine-based additive in the cuvette is exposed to a UV and/or visible light source. Using a spectrometer, the count value of the isolated sample's fluorescence spectrum at its peak value is measured.

DETAILED DESCRIPTION OF THE INVENTION

Figure 1:
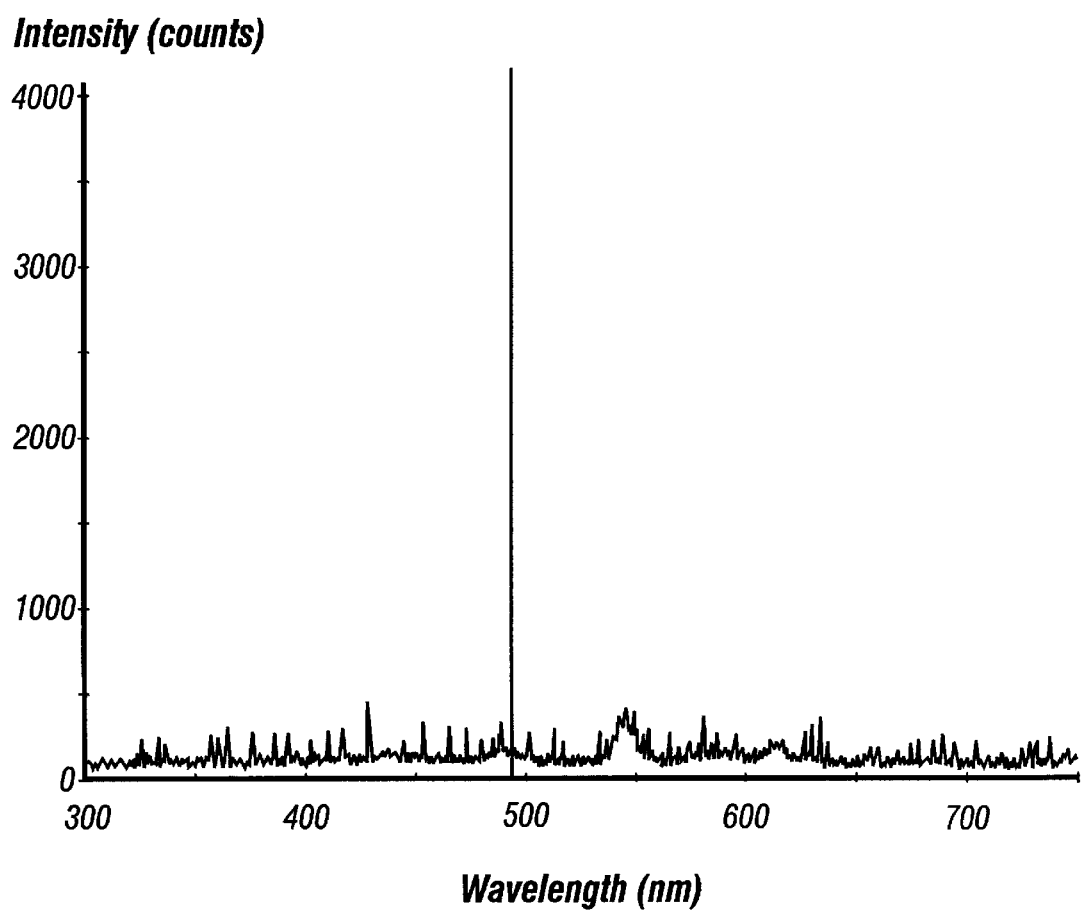
FIG. 1 is an example of the blank background fluorescence spectrum in one embodiment of this invention.

Because many additives for aqueous fluids (such as those used in hydrocarbon recovery) are relatively expensive, it is desirable to only use as much additive as is necessary to achieve the desired purpose. However, it is also necessary to determine that enough additive is present to achieve the purpose for which it is used, and/or to determine that the additive is still effective.

In trying to devise a method for determining the presence of amine-based clay stabilizers in aqueous drilling fluids, it was surprisingly discovered that after isolating a clay stabilizer sample, that a fluorescent light count obtained by spectrometer reading of the sample would give a quantitative value (via a simple linear equation) of the amount of amine-based clay stabilizer in the fluid.

The inventive method described herein is expected to be applicable to test for amine-based compounds in aqueous drilling fluids in general, which may be used as clay stabilizers, corrosion inhibitors, surfactants, and the like. In one non-limiting embodiment of the invention, the amine-based additives which are clay stabilizers are an aqueous blend of amine-acetate salts. One commercially available aqueous, but complex blend of amine-acetate salts is CLAY-TROL™ clay stabilizer available from Baker Hughes INTEQ. Although the term CLAY-TROL is used herein for brevity, the invention is not limited to this product and it is expected that the method of this invention would be applicable to determine the presence of any amine-based fluid additive.

An original test procedure for CLAY-TROL involved an extraction method using a phenolphthalein indicator. However, test results were obscured by the presence of lignosulfonate and lignite, which were intentionally used as two primary dispersants in the particular lime hybrid mud system in question. Because this method was unsatisfactory, the drilling mud consultants involved relied upon a retort method to determine CLAY-TROL content. This procedure had been used successfully in the past on mud jobs using clay stabilizers of other chemistries. However, the CLAY-TROL treatment level was still excessive (up to 12 lb/bbl (34 g/l)). There were also concerns expressed about whether CLAY-TROL was truly available to provide shale stabilization.

Initial investigative efforts were made to improve the original phenolphthalein test, but with limited results. Work then began on spectrographic analysis at visible light wavelengths. After not accomplishing much success with that particular approach either, it was accidentally discovered that the isolated samples fluoresced, and subsequently, that a linear correlation could be found between the spectrometric count at a particular, peak wavelength and the amount of CLAY-TROL present.

It can be appreciated that for somewhat different chemistries the optimum wavelength to take measurements may be different, and the linear or other equation to determine the amount of clay stabilizer would be different. Nevertheless, it is expected that one of ordinary skill in the art could readily determine these values and equations using a similar technique to what is described below. That is, the peak wavelength of the fluorescent spectrum for a particular amine chemistry may be empirically observed, and the exact equation determined by linear regression analysis. The light source may be ultraviolet (UV) or visible fight as necessary to cause the sample to fluoresce. The fluorescent spectrum of the sample to be measured may have a peak between about 300 to about 800 nm.

The general formula for expressing the linear relationship of the inventive method is $$\text{Amount} = \frac{\text{Count} - \text{Intercept}}{\text{Slope}}$$

As noted, determining the values for the intercept and slope for a particular amine-based chemistry is a matter of routine linear regression analysis.

Briefly stated, a method has been discovered to determine residual CLAY-TROL, even in the presence of lignosulfonate and/or lignite. A fluorescence test procedure for determining residual CLAY-TROL in filtrates containing lignosulfonate and/or lignite was found to provide reproducible and reliable results. Even with varying lignosulfonate concentrations, residual CLAY-TROL as low as 1 lb/bbl (2.86 g/l) could be measured reproducibly. More specifically, the method for determining the presence of CLAY-TROL is as follows, with reference to FIGS. 1–3:

Standard Method for the Determination of CLAY-TROL in Drilling Fluid Filtrates

I. Introduction

A filtrate sample is extracted with a chlorinated solvent to isolate the CLAY-TROL component from the aqueous phase. The concentration of CLAY-TROL is determined by its fluorescence property using an Ocean Optics SD2000 Spectrometer, for example.

II. Equipment

Ocean Optics SD2000 Spectrometer connected to the serial port of a personal or other computer Solvent Extraction Vial 5 ml Mohr or Serological Pipet Disposable Transfer Pipets Fluorescence cuvettes, 10 mm Chloroform (trichloromethane)

III. Procedure

A. CLAY-TROL Isolation

1. Prepare Solvent Extraction Vial by placing 4 ml of chloroform in vial.
2. Obtain mud sample and adjust the pH to above 9 if necessary.
3. Obtain 5 ml or more filtrate using standard API press.
4. Place 3 ml of filtrate in Solvent Extraction Vial and mix vigorously for 2 minutes.
5. Allow phases to separate, centrifuge if necessary.

B. CLAY-TROL Measurement

1. Prepare fluorescence spectrometer and computer.
2. Remove the top water phase and place chloroform ($CHCl_3$) solution in Fluorescence cuvette.
3. Cap the cuvette and place in Cuvette Holder on the DT-1000 Light Source.
4. Cover with box and allow fluorescence spectrum on the computer screen to stabilize. Computer visuals will change from something like FIG. 1 to something like FIG. 2.
5. With the cursor placed at 494 nm, read and record the count value at the bottom left of the computer screen. Computer visual should be like FIG. 3.
6. The count intensity is related to the CLAY-TROL concentration in pounds per barrel (ppb) using the equation:

$$\text{CLAY-TROL}, ppb = \frac{\text{Count value} - 322}{459}$$

To obtain the concentration in units of grams per liter, the above fraction should be multiplied by 2.86.

Figure 2:
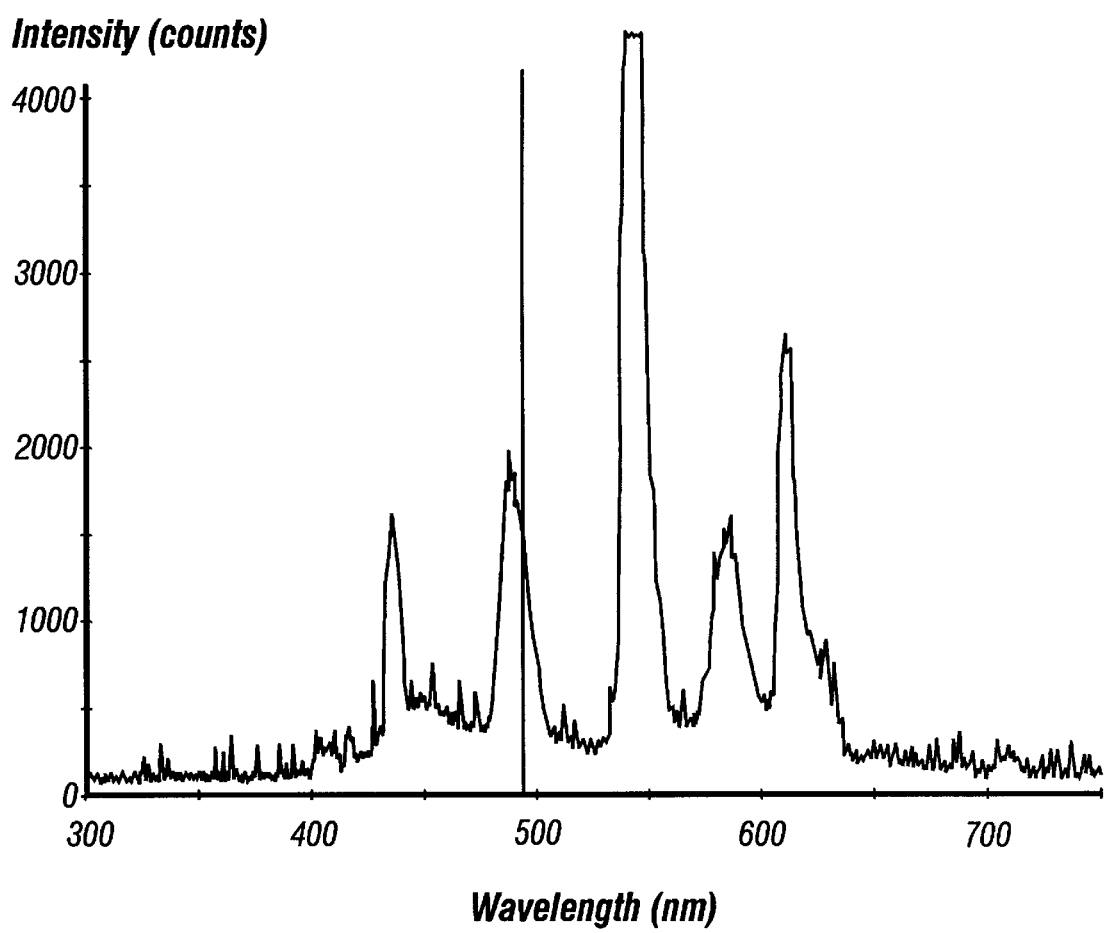
FIG. 2 is an example of a signal from background fluorescent lights using the spectrometer used for FIG. 1.
Figure 3:
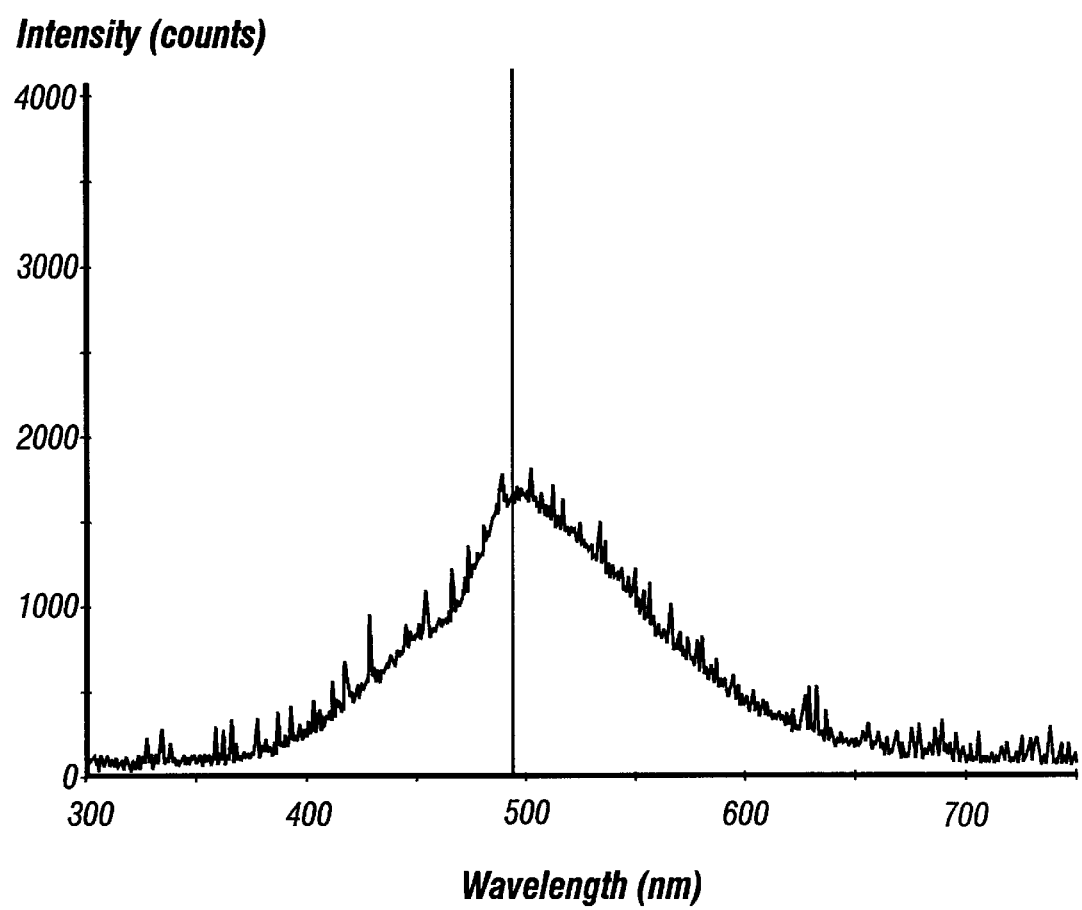
FIG. 3 is an example of an amine-based additive fluorescence spectrum in one embodiment of this invention indicating how the intensity (counts) may be measured at a peak wavelength (494 nm)

It should be understood that the spectrum observed such as shown in FIG. 2 is simply the background spectrum of what in this case were overhead fluorescent light fixtures. Once this background light is blocked, the wavelength fluorescing from the sample may be observed.

It will be appreciated that this is a very specific procedure, and that the inventive method is not limited to this exact procedure. The above Standard Method could be varied in a number of respects to achieve essentially the same result. For instance, the pH of the mud sample could be adjusted using an suitable reagent including, but not necessarily limited to NaOH, KOH, lime, and the like. Other water immiscible solvents besides chloroform could be used, for example, dichloromethane, carbon tetrachloride, trichloroethylene, ether, hexane, octanol, and the like, and mixtures thereof, such as a mixture of chloroform and hexane, and the like. In one non-limiting embodiment of the invention, halogenated solvents are preferred. The filtrate could be added to the Solvent Extraction Vial prior to the addition of the halogenated solvent. Certainly the equipment could be varied from that specified, as long as the equipment can perform the necessary functions. Further, the exact peak wavelength and the linear formula of the last step will vary according to the exact chemistry of the amine-based additive.

Figure 4:
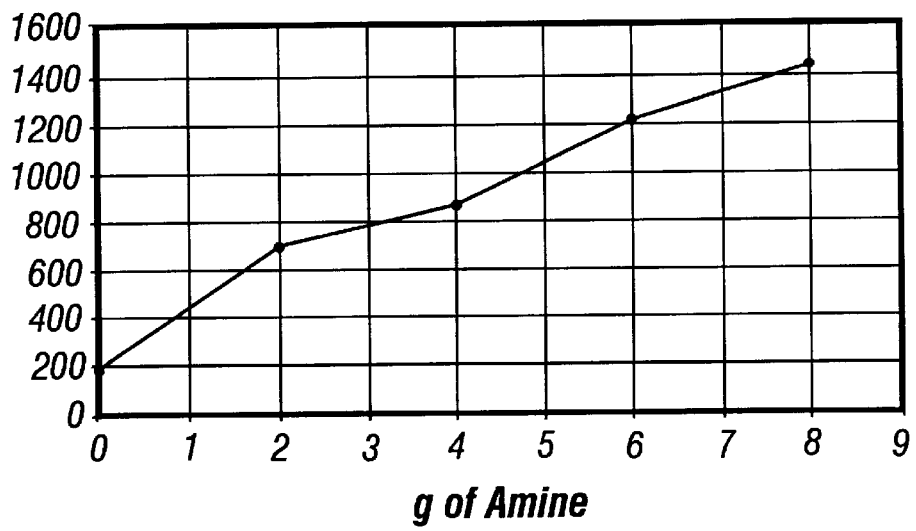
FIG. 4 is a graph of increasing fluorescence with increasing proportion of amine-based additive (in grams) in an aqueous 350 ml brine solution of 11% NaCl containing 7 g of lignosulfonate at a pH of 11.

When the fluorescent characteristic of CLAY-TROL was first discovered, synthetic filtrates containing varying amounts of CLAY-TROL with and without lignosulfonate were submitted to a Baker Petrolite laboratory equipped with a UV/visible light spectrometer. Results showed that it appeared to be possible to quantify an amine mix in a drilling fluid filtrate by fluorescence. It was additionally discovered that varying amounts of lignosulfonate did not interfere with CLAY-TROL amine results. The results are shown in FIG. 4.

Figure 5:
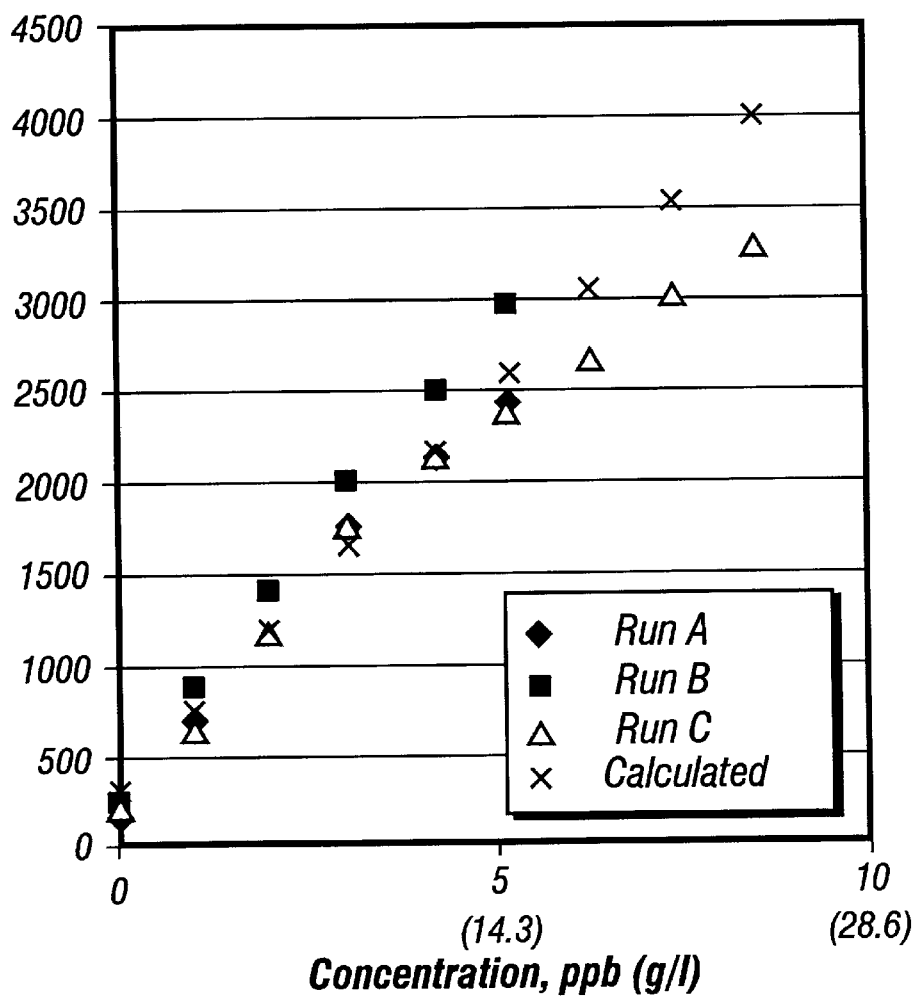
FIG. 5 is a graph of increasing fluorescence with increasing proportion of CLAY-TROL (in ppb) for three runs and a calculated average.

Based on these promising results, INTEQ Laboratories obtained a UV and visible spectrometer to continue fluorescent studies. Fluorescent data from three experiment matrices were entered into a spread sheet and a linear regression calculation performed. Experimental test matrices included two runs of increasing CLAY-TROL content in 11% NaCl solutions with pH level adjusted to 11; specific source of CLAY-TROL (denoted in Table I as Runs A and C) was used. The third test used another source of CLAY-TROL (denoted in Table I as Run B). Experimental fluorescent data were as shown in Table I and plotted in FIG. 5.

TABLE 1

Fluorescent Readings

| CLAY-TROL, | | Run A, nm | Run B, nm | Run C, nm | |
|---|---|---|---|---|---|
| lb/bbl | g/l | reading | reading | reading | Calculated |
| 0 | 0 | 135 | 135 | 135 | 322 |
| 1 | 2.9 | 672 | 830 | 715 | 781 |
| 2 | 5.7 | 1259 | 1398 | 1260 | 1240 |
| 3 | 8.6 | 1688 | 1997 | 1700 | 1699 |
| 4 | 11.4 | 2135 | 2510 | 2110 | 2158 |
| 5 | 14.3 | 2424 | 2940 | 2360 | 2617 |
| 6 | 17.2 | | | 2655 | 3076 |
| 7 | 20.0 | | | 3020 | 3535 |
| 8 | 22.9 | | | 3220 | 3994 |

The results showed a $r^2$ of 0.946 and gave the equation:

$$\text{CLAY-TROL amount}, ppb = \frac{\text{Count value} - 322}{459}$$

This equation is used in the Standard Method outlined above. (Again, to obtain the CLAY-TROL amount in g/l units, the fraction on the right side of the should be multiplied by 2.86.)

Intensive studies confirmed the fluorescent method to work, in spite of the presence of lignosulfonate and/or lignite, as shown in the following Table III:

TABLE II

Residual CLAY-TROL Content As Determined by Fluorescence

| UNI-CAL, | | LIGCO, | | CLAY-TROL, (calculated) | |
|---|---|---|---|---|---|
| lb/bbl | g/l | lb/bbl | g/l | lb/bbl | g/l |
| 0 | 0 | 0 | 0 | 3.4 | 9.7 |
| | (base fluid) | | (base fluid) | | |
| 3.5 | 10 | 0 | 0 | 3.5 | 10 |
| 7 | 20 | 0 | 0 | 3.2 | 9.2 |
| 0 | 0 | 2 | 5.7 | 3.2 | 9.2 |
| 7 | 20 | 7 | 20 | 2.6 | 7.4 |
| 7 | 20 | 10 | 28.6 | 3.4 | 9.7 |
| 7 | 20 | 20 | 57.2 | 3.0 | 8.6 |

Filtrate studies of CLAY-TROL mud samples from two different locations were conducted with the inventive fluorescence method. One was an All-Polymer Mud system, while the other was a Lime Hybrid Mud system. Chemical concentration spread sheets were obtained for both muds. The All-Polymer Mud was shown to have less than 1 lb/bbl residual (2.86 g/l) CLAY-TROL. This was also confirmed using an alternative method.

The Lime Hybrid Mud was included in a mud make-up, but no lignosulfonate or lignite was added. After collecting the base filtrate, the Lime Hybrid Mud was treated with varying concentrations of UNI-CAL® and LIGCO® (with caustic treatment to maintain original mud pH ranging between 10.9 and 11.0). Filtrates were obtained and CLAY-TROL concentrations were determined using the inventive method; specifically the Standard Method described above. Results showed the fluorescent method to work, in spite of the presence of lignosulfonate and/or lignite.

The fluorescence procedure of the invention utilizing a laptop or other computer set up with a spectrometer and light source can be easily installed in a regional laboratory. Collected mud samples can be delivered on a timely basis, knowing the offshore transportation frequency to rigs. If more immediate on-site rig answers are needed, this procedure will require special housing conditions, such as possible installation in the logging unit to minimize the rigors of rig conditions (e.g. weather, vibrations, power surges, etc.) due to the relative sophistication of the test equipment.

In the foregoing specification, the invention has been described with reference to specific embodiments thereof, and has been demonstrated as effective in providing a reproducible method for testing the quantity of amine-based fluid additives in aqueous fluid systems, such as drilling fluids, drill-in fluids, and completion fluids. Additionally, the method of this invention is expected to be useful in determining the presence and concentration of amine-based additives in non-aqueous fluids as well, with the expected modifications. Further, it will be evident that various modifications and changes can be made to the inventive method without departing from the broader spirit or scope of the invention as set forth in the appended claims. Accordingly, the specification is to be regarded in an illustrative rather than a restrictive sense. For example, specific systems of brines, amine-based additives, lignosulfonates and lignites, and other common drilling system additives, falling within the claimed parameters, but not specifically identified or tried in a particular method, are anticipated to be within the scope of this invention. Similarly, routine modifications of the inventive test method, such as by using a different solvent extractant or different test equipment would be expected to fall within the scope of the invention.

Glossary

LIGCO® A lignite material available from Baker Hughes INTEQ.
UNI-CAL® A lignosulfonate material available from Baker Hughes INTEQ.

We claim:

1. A method for determination of amine-based additive in a fluid, the method comprising:
    isolating the amine-based additive from a fluid filtrate sample;
    placing the amine-based additive in a cuvette;
    exposing the amine-based additive in the cuvette to a UV light source; and
    measuring the count value of the isolated sample's fluorescence spectrum at its peak using a spectrometer.

2. The method of claim 1 where the amine-based additive is an amine-based clay stabilizer.

3. The method of claim 2 where the clay stabilizer is an amine-acetate salt-based clay stabilizer.

4. The method of claim 1 where the count value of the sample's fluorescence spectrum is taken at a value between 300 and 800 nm.

5. The method of claim 4 where the amount of amine-based additive is quantified according to the equation:

$$\text{Amount} = \frac{\text{Count} - \text{Intercept}}{\text{Slope}}.$$

6. The method of claim 1 where isolating the amine-based additive further comprises extracting it from the fluid filtrate sample with a water immiscible solvent.

7. The method of claim 6 where isolating the amine-based additive further comprises:
    obtaining a fluid filtrate sample containing the amine-based additive;
    mixing the fluid filtrate with a water immiscible solvent in a container to form a mixture;
    allowing phases of the mixture to separate, and
    removing at least a portion of a top water phase.

8. The method of claim 7 where the water immiscible solvent is a halogenated solvent.

9. The method of claim 1 where in the isolating of the amine-based additive, there is still present a material selected from the group consisting of a lignosulfonate and a lignite.

10. The method of claim 1 where the fluid is an aqueous fluid used for hydrocarbon recovery and is selected from the group consisting of drilling fluids, drill-in fluids, and completion fluids.

11. A method for determination of an amine-based additive in a fluid used for hydrocarbon recovery, the method comprising:
    isolating the amine-based additive from a fluid filtrate sample by extraction with a water immiscible solvent;
    placing the amine-based additive in a cuvette;
    exposing the amine-based additive in the cuvette to a UV light source; and
    measuring the count value of the isolated sample's fluorescence spectrum at its peak between 300–800 nm using a spectrometer.

12. The method of claim 11 where in the isolating of the amine-based additive, there is still present a material selected from the group consisting of a lignosulfonate and a lignite.

13. The method of claim 11 where the fluid is an aqueous fluid and is selected from the group consisting of drilling fluids, drill-in fluids, and completion fluids.

14. The method for determination of amine-acetate salt-based additive in an aqueous fluid for hydrocarbon recovery, the method comprising:
    isolating the amine-acetate salt-based additive from a drilling fluid filtrate sample by:
        obtaining a fluid filtrate containing the additive;
        mixing the fluid filtrate with a water immiscible solvent in a container to from a mixture;
        allowing phases of the mixture to separate, and
        removing at least a portion of a top water phase;
    placing the amine-acetate salt-based additive in the top water phase portion in a cuvette;
    exposing the amine-acetate salt-based additive in the cuvette to a UV light source; and
    measuring the count value of the isolated sample's fluorescence spectrum at a value between 300–800 nm using a spectrometer.

15. The method of claim 14 where the amount of additive is quantified according to the equation:

$$\text{Amount} = \frac{(\text{Count}) - 322}{459}.$$

16. The method of claim 14 where the water immiscible solvent is a halogenated solvent.

17. The method of claim 14 where in the isolating of the additive, there is still present a material selected from the group consisting of a lignosulfonate and a lignite.

18. The method of claim 1 where the aqueous fluid for hydrocarbon recovery is selected from the group consisting of drilling fluids, drill-in fluids, and completion fluids.

* * * * *